(12) United States Patent
Naughton et al.

(10) Patent No.: US 10,936,626 B1
(45) Date of Patent: *Mar. 2, 2021

(54) DATABASE AND DATA PROCESSING SYSTEM FOR USE WITH A NETWORK-BASED PERSONAL GENETICS SERVICES PLATFORM

(71) Applicant: 23andMe, Inc., Sunnyvale, CA (US)

(72) Inventors: Brian Thomas Naughton, Mountain View, CA (US); Chuong Do, Mountain View, CA (US); John Michael Macpherson, Santa Ana, CA (US)

(73) Assignee: 23andMe, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/874,495

(22) Filed: May 14, 2020

Related U.S. Application Data

(63) Continuation of application No. 16/554,212, filed on Aug. 28, 2019, now Pat. No. 10,691,725, which is a
(Continued)

(51) Int. Cl.
*G06F 16/28* (2019.01)
*G16B 50/00* (2019.01)
(Continued)

(52) U.S. Cl.
CPC .......... *G06F 16/284* (2019.01); *G16B 20/00* (2019.02); *G16B 50/00* (2019.02); *G16H 10/60* (2018.01); *G16H 50/30* (2018.01)

(58) Field of Classification Search
CPC ........ G16H 50/20; G16H 10/60; G16H 50/30; G16H 50/70; G16H 10/40; G16H 50/50;
(Continued)

(56) References Cited

U.S. PATENT DOCUMENTS 5,288,644 A  2/1994  Beavis et al.
5,384,261 A  1/1995  Winkler et al.
(Continued)

FOREIGN PATENT DOCUMENTS

WO    WO 90/15070 A1   12/1990
WO    WO 92/10092 A1    6/1992
(Continued)

OTHER PUBLICATIONS

Preliminary Amendment dated Aug. 4, 2017 filed in U.S. Appl. No. 15/621,985.
(Continued)

*Primary Examiner* — Mary K Zeman
(74) *Attorney, Agent, or Firm* — Weaver Austin Villeneuve & Sampson LLP; David K. Buckingham

(57) ABSTRACT

Databases and data processing systems for use with a network-based personal genetics services platform may include member information pertaining to a plurality of members of the network-based personal genetics services platform. The member information may include genetic information, family history information, environmental information, and phenotype information of the plurality of members. A data processing system may determine, based at least in part on the member information, a model for predicting a phenotype from genetic information, family history information, and environmental information, wherein determining the model includes training the model using the member information pertaining to a set of the plurality of members. The data processing system may also receive a request from a questing member to predict a phenotype of interest, and apply an individual's genetic information, family history information, and environmental information to the model to obtain a prediction associated with the phenotype of interest for the requesting member.

28 Claims, 5 Drawing Sheets

Related U.S. Application Data continuation of application No. 15/151,404, filed on May 10, 2016, now Pat. No. 10,437,858, which is a continuation of application No. 13/304,091, filed on Nov. 23, 2011, now abandoned.

(51) Int. Cl.
  *G16B 20/00* (2019.01)
  *G16H 50/30* (2018.01)
  *G16H 10/60* (2018.01)

(58) Field of Classification Search
  CPC ........ G16H 80/00; G16H 40/67; G16H 15/00; G16H 40/63; G16H 50/00; C12Q 1/6883; C12Q 2600/156; C12Q 2600/118; C12Q 2600/106; C12Q 2600/112; C12Q 1/6827; C12Q 2537/165; C12Q 2600/172; C12Q 1/68; C12Q 1/6809; G06N 20/00; G06N 3/08; G06N 7/005; G06N 5/02; G06N 20/10; G06N 20/20; G06N 3/0454; G06N 7/00; G06N 5/003; G06N 5/022; G06N 3/088; G06N 5/025; G06N 5/04; G06N 5/048; G06N 3/0427; G01N 2800/52; G01N 2800/60; G01N 2570/00; G01N 2800/50; G01N 33/57407; G01N 2800/56; G06F 19/00; G06F 16/9535; G06F 17/18; G06F 16/2365; G06F 16/284; G06F 16/2465; G06F 16/51; G06F 16/9024; G06F 16/90328; G06F 16/906; G06F 2216/03; Y02A 90/26; G16C 20/70; G16B 20/00; G16B 40/00; G16B 30/00; G16B 50/00; G16B 20/20; G16B 40/20; G16B 40/30; G16B 50/30; G16B 20/10; G16B 5/00; G16B 5/20; G16B 20/40; G16B 30/10; G16B 45/00; G06Q 40/08; G06Q 50/24; G06K 9/00228; G06K 9/6256; G06K 9/6267; C40B 40/08

See application file for complete search history.

(56) References Cited

U.S. PATENT DOCUMENTS

| | | | |
|---|---|---|---|
| 5,424,186 A | 6/1995 | Fodor et al. | |
| 5,692,501 A | 12/1997 | Minturn | |
| 7,062,752 B2 | 6/2006 | Simpson et al. | |
| 7,076,504 B1 | 7/2006 | Handel et al. | |
| 7,630,986 B1 | 12/2009 | Herz et al. | |
| 7,783,665 B1 | 8/2010 | Tormasov et al. | |
| 7,818,396 B2 | 10/2010 | Dolin et al. | |
| 7,951,078 B2 | 5/2011 | Scheuner | |
| 7,957,907 B2 | 6/2011 | Sorenson et al. | |
| 8,156,158 B2 | 4/2012 | Rolls et al. | |
| 8,187,811 B2 | 5/2012 | Eriksson et al. | |
| 8,428,886 B2 | 4/2013 | Wong et al. | |
| 8,463,554 B2 | 6/2013 | Hon et al. | |
| 8,510,057 B1 * | 8/2013 | Avey ................... | G16B 20/00 702/19 |
| 8,543,339 B2 | 9/2013 | Wojcicki et al. | |
| 8,589,437 B1 | 11/2013 | Khomenko et al. | |
| 8,645,343 B2 | 2/2014 | Wong et al. | |
| 8,719,045 B2 | 5/2014 | Yoon et al. | |
| 8,738,297 B2 | 5/2014 | Sorenson et al. | |
| 8,744,982 B2 | 6/2014 | Crockett et al. | |
| 8,786,603 B2 | 7/2014 | Rasmussen et al. | |
| 8,855,935 B2 | 10/2014 | Myres et al. | |
| 8,990,198 B2 | 3/2015 | Rolls et al. | |
| 8,990,250 B1 | 3/2015 | Chowdry et al. | |
| 9,092,391 B2 | 7/2015 | Stephan et al. | |
| 9,116,882 B1 | 8/2015 | Macpherson et al. | |
| 9,213,944 B1 | 12/2015 | Do et al. | |
| 9,213,947 B1 | 12/2015 | Do et al. | |
| 9,218,451 B2 | 12/2015 | Wong et al. | |
| 9,336,177 B2 | 5/2016 | Hawthorne et al. | |
| 9,367,663 B2 | 6/2016 | Deciu et al. | |
| 9,367,800 B1 | 6/2016 | Do et al. | |
| 9,390,225 B2 | 7/2016 | Barber et al. | |
| 9,405,818 B2 | 8/2016 | Chowdry et al. | |
| 9,836,576 B1 | 12/2017 | Do et al. | |
| 9,864,835 B2 | 1/2018 | Avey et al. | |
| 9,984,198 B2 | 5/2018 | Deciu et al. | |
| 10,249,389 B2 * | 4/2019 | Athey .................... | A61K 31/37 |
| 10,437,858 B2 * | 10/2019 | Naughton ............. | G16H 10/60 |
| 10,553,318 B2 * | 2/2020 | Athey .................... | G16B 40/00 |
| 10,691,725 B2 * | 6/2020 | Naughton ............. | G16B 10/60 |
| 10,841,312 B2 | 11/2020 | Hawthorne et al. | |
| 10,854,318 B2 | 12/2020 | Macpherson et al. | |
| 10,891,317 B1 | 1/2021 | Chowdry et al. | |
| 2002/0019746 A1 | 2/2002 | Rienhoff et al. | |
| 2002/0128860 A1 | 9/2002 | Leveque et al. | |
| 2002/0138572 A1 | 9/2002 | Delany et al. | |
| 2003/0113727 A1 | 6/2003 | Girn et al. | |
| 2003/0129630 A1 | 7/2003 | Aakalu et al. | |
| 2004/0093334 A1 | 5/2004 | Scherer | |
| 2005/0003410 A1 | 1/2005 | Frazer et al. | |
| 2005/0027560 A1 | 2/2005 | Cook | |
| 2005/0152905 A1 | 7/2005 | Omoigul | |
| 2005/0164704 A1 | 7/2005 | Winsor | |
| 2006/0064415 A1 | 3/2006 | Guyon et al. | |
| 2006/0257903 A1 | 11/2006 | Akil et al. | |
| 2007/0027917 A1 | 2/2007 | Ariel et al. | |
| 2007/0061085 A1 | 3/2007 | Fernandez | |
| 2007/0226250 A1 | 9/2007 | Mueller et al. | |
| 2008/0021288 A1 | 1/2008 | Bowman et al. | |
| 2008/0082955 A1 | 4/2008 | Andreessen et al. | |
| 2008/0091471 A1 | 4/2008 | Michon et al. | |
| 2008/0097938 A1 | 4/2008 | Guyon et al. | |
| 2008/0131887 A1 | 6/2008 | Stephan et al. | |
| 2008/0162510 A1 | 7/2008 | Baio et al. | |
| 2008/0201174 A1 | 8/2008 | Ramasubramanian et al. | |
| 2008/0228797 A1 | 9/2008 | Kenedy et al. | |
| 2008/0286796 A1 | 11/2008 | Grupe et al. | |
| 2009/0043752 A1 | 2/2009 | Kenedy et al. | |
| 2009/0077110 A1 | 3/2009 | Petri | |
| 2009/0099789 A1 | 4/2009 | Stephan et al. | |
| 2009/0112871 A1 | 4/2009 | Hawthorne et al. | |
| 2009/0119083 A1 | 5/2009 | Avey et al. | |
| 2009/0132284 A1 | 5/2009 | Fey et al. | |
| 2009/0186347 A1 | 7/2009 | Cox et al. | |
| 2009/0299645 A1 | 12/2009 | Colby et al. | |
| 2010/0042438 A1 | 2/2010 | Moore et al. | |
| 2010/0070455 A1 | 3/2010 | Halperin et al. | |
| 2011/0098187 A1 | 4/2011 | Urdea et al. | |
| 2011/0098193 A1 | 4/2011 | Kingsmore et al. | |
| 2012/0270794 A1 | 10/2012 | Eriksson et al. | |
| 2013/0129630 A1 | 5/2013 | Haik | |
| 2013/0230858 A1 | 9/2013 | Cantor et al. | |
| 2013/0345988 A1 | 12/2013 | Avey et al. | |
| 2014/0006433 A1 | 1/2014 | Hon et al. | |
| 2014/0067355 A1 | 3/2014 | Noto et al. | |
| 2016/0026755 A1 | 1/2016 | Byrnes et al. | |
| 2016/0103950 A1 | 4/2016 | Myres et al. | |
| 2016/0171155 A1 | 6/2016 | Do et al. | |
| 2016/0186266 A1 | 6/2016 | Alarcon | |
| 2016/0277408 A1 | 9/2016 | Hawthorne et al. | |
| 2016/0350479 A1 | 12/2016 | Han et al. | |
| 2017/0011042 A1 | 1/2017 | Kermany et al. | |
| 2017/0017752 A1 | 1/2017 | Noto et al. | |
| 2017/0220738 A1 | 8/2017 | Barber et al. | |
| 2017/0228498 A1 | 8/2017 | Hon et al. | |
| 2017/0277827 A1 | 9/2017 | Granka et al. | |
| 2017/0277828 A1 | 9/2017 | Avey et al. | |
| 2017/0329866 A1 | 11/2017 | Macpherson | |
| 2017/0329891 A1 | 11/2017 | Macpherson et al. | |
| 2017/0329899 A1 | 11/2017 | Bryc et al. | |
| 2017/0329901 A1 | 11/2017 | Chowdry et al. | |
| 2017/0329902 A1 | 11/2017 | Bryc et al. | |
| 2017/0329904 A1 | 11/2017 | Naughton et al. | |
| 2017/0329915 A1 | 11/2017 | Kittredge et al. | |

(56) References Cited

U.S. PATENT DOCUMENTS

| | | | |
|---|---|---|---|
| 2017/0329924 A1* | 11/2017 | Macpherson | G16B 20/20 |
| 2017/0330358 A1 | 11/2017 | Macpherson et al. | |
| 2019/0017119 A1 | 1/2019 | Khera et al. | |
| 2019/0330698 A1 | 10/2019 | Khera et al. | |
| 2019/0341125 A1 | 11/2019 | Khera et al. | |
| 2019/0345557 A1 | 11/2019 | Khera et al. | |
| 2019/0345566 A1 | 11/2019 | Khera et al. | |
| 2019/0384777 A1 | 12/2019 | Naughton et al. | |
| 2020/0118647 A1 | 4/2020 | Zhang et al. | |
| 2020/0153296 A1* | 5/2020 | Albieri | H02K 1/2766 |
| 2020/0372974 A1 | 11/2020 | Chowdry et al. | |

FOREIGN PATENT DOCUMENTS

| | | |
|---|---|---|
| WO | WO 2008/067551 | 6/2008 |
| WO | WO 2010/139006 | 12/2010 |
| WO | WO 2016/073953 | 5/2016 |

OTHER PUBLICATIONS

U.S. Office Action dated Dec. 22, 2010 in U.S. Appl. No. 12/151,977.
U.S. Final Office Action dated Jul. 18, 2011 in U.S. Appl. No. 12/151,977.
U.S. Office Action dated Oct. 24, 2011 in U.S. Appl. No. 12/151,977.
U.S. Final Office Action dated Mar. 19, 2012 in U.S. Appl. No. 12/151,977.
U.S. Notice of Allowance dated Apr. 3, 2013 in U.S. Appl. No. 12/151,977.
U.S. Notice of Allowance dated Jul. 11, 2013 in U.S. Appl. No. 12/151,977.
U.S. Office Action dated May 19, 2015 in U.S. Appl. No. 13/932,513.
U.S. Final Office Action dated Jan. 11, 2016 in U.S. Appl. No. 13/932,513.
U.S. Office Action dated Dec. 13, 2016 in U.S. Appl. No. 13/932,513.
U.S. Office Action dated Apr. 17, 2019 in U.S. Appl. No. 15/621,985.
U.S. Final Office Action dated Jan. 22, 2020 in U.S. Appl. No. 15/621,985.
U.S. Office Action dated Sep. 27, 2018 in U.S. Appl. No. 15/151,404.
U.S. Notice of Allowance dated Jun. 10, 2019 in U.S. Appl. No. 15/151,404.
U.S. Office Action dated Oct. 25, 2019 in U.S. Appl. No. 16/554,212.
U.S. Notice of Allowance dated Feb. 14, 2020 in U.S. Appl. No. 16/554,212.
Morrison, A. C., et al. "Prediction of Coronary Heart Disease Risk using a Genetic Risk Score: The Atherosclerosis Risk in Communities Study," American Journal of Epidemiology, vol. 166, No. 1, Apr. 18, 2007, pp. 28-35.
Schabath, M.B., et al. "Cancer Epidemiology, Biomarkers & Prevention: Combined Effects of the p53 and p73 Polymorphisms on Lung Cancer Risk," Cancer Epidemiol Biomarkers Prev., Jan. 24, 2006, vol. 15, pp. 158-161. [doi: 10.1158/1055-9965.EPI-05-0622].
Scheuner, et al., "Family History: A Comprehensive Genetic Risk Assessment Method for the Chronic Conditions of Adulthood" American Journal of Medical Genetics, Wiley-Liss, Inc., vol. 71, 1997, pp. 315-324.
Yoon, et al., "Developing Family Healthware, a Family History Screening Tool to Prevent Common Chronic Diseases" Preventing Chronic Disease: Public Health Research, Practice, and Policy, vol. 6, No. 1, Jan. 2009, pp. 1-11.
Mealiffe, et al., "Assessment of Clinical Validity of a Breast Cancer Risk Model Combining Genetic and Clinical Information" J. Natl. Cancer Institute (JNCI), vol. 102, No. 21, Nov. 3, 2010, pp. 1618-1627.
Ruderfer, et al., "Family-based genetic risk prediction of multifactorial disease" Genome Medicine, vol. 2:1, Jan. 15, 2010, pp. 1-7. <doi:10.1186/gm123>.
Lyssenko, M.D., et al., "Clinical Risk Factors, DNA Variants, and the Development of Type 2 Diabetes" The New England Journal of Medicine, vol. 359, Nov. 20, 2008, pp. 2220-2232. <doi:10.1056/NEJMoa0801869>.
Tung, et al., "Efficient Replication of over 180 Genetic Associations with Self-Reported Medical Data" PLoS One, vol. 6, No. 8, e23473, Aug. 17, 2011, pp. 1-9. <doi: 10.1371/journal.pone.0023473>.
Polymeropoulos et al. "Mutation in the alpha-synuclein gene identified in families with Parkinson's disease" Science 276 (1997) pp. 2045-2047.
Kruger et al. "Ala30Pro mutation in the gene encoding alpha-synuclein in Parkinson's disease".
Abbas et al. "A wide variety of mutation in the parkin gene are responsible for autosomal recessive parkinsonism in Europe" Hum. Mol. Genet., vol. 8, No. 4 (1999) pp. 567-574.
Lucking et al., "Association Between Early-Onset Parkinson's Disease and Mutations in the Parkin Gene" N. Engl. J. Med. 342, May 2000, pp. 1560-1567.
International Schizophrenia Consortium et al. "Common polygenic variation contributes to risk of schizophrenia and bipolar disorder" Nature 460(7256) (2009) pp. 748-752.
Hoggart et al. "Simultaneous analysis of all SNPs in genome-wide and re-sequencing association studies" PLoS Genet. 4(7) (2008) e1000130.
Wu et al. "Genome-wide association analysis by lasso penalized logistic regression" Bioinformatics 25(6) (2009) pp. 714-721.
Kim et al. "A multivariate regression approach to association analysis of a quantitative trait network" Bioinformatics 25(12)(2009) pp. i204-212.
Castets et al. "Zinedin, SG2NA, and striatin are calmodulin-binding, WD repeat proteins principally expressed in the brain" J. Biol. Chem. 275, (2000) pp. 19970-19977.
Purcell et al. "PLINK: a toolset for whole-genome association and population-based linkage analysis" Am. J. Hum. Genet., vol. 81, Sep. 2007, pp. 559-575.
International HapMap Consortium "A second generation human haplotype map of over 3.1 million SNPs" Nature 449(764) Oct. 18, 2007, pp. 851-861.
Guan and Stephens, "Practical issues in imputation-based association mapping" PLoS Genet. 4(12) Dec. 2008, e100279, pp. 1-11.
Devlin and Roeder, "Genomic control for association studies" Biometrics 55(4) (1999) pp. 997-1004.
Altshuler et al. "Genetic mapping in human disease" Science 322(5903) (2009) pp. 881-888.
Healy et al. "Phenotype, genotype, and worldwide genetic penetrance of LRRK2-associated Parkinson's disease: a case-control study" Lancet Neurol. 7(7) (2008) pp. 583-590.
Hirschhorn J.N., "Genomewide Association Studies—Illuminating Biologic Pathways" N. Engl. J. Med. 360 (2009) pp. 1699-1701.
Grünblatt et al., "Gene expression profiling of parkinsonian substantia nigra pars compacta: alterations in ubiquitin-proteasome, heat shock protein, iron and oxidative stress regulated proteins, cell adhesion/cellular matrix and vesicle trafficking genes" J. Neural Transm 111(12) (2004) pp. 1543-1573.
Reczek D. et al., "LIMP-2 Is a Receptor for Lysosomal Mannose-6-Phosphate-Independent Targeting of beta-Glucocerebrosidase" Cell Nov. 16; 131(4) (2007) pp. 770-783.
Sidransky E. et al. "Multicenter Analysis of Glucorcerebrosidase Mutations in Parkinson's Disease" NEJM vol. 361 (2009) pp. 1651-1661.
NCBI Reference SNP Cluster Report: rs10513789. Nov. 2003.
NCBI Reference SNP Cluster Report: rs10513789. Nov. 2003. pp. 1-6. [Retrieved from the internet, May 2, 2011] <URL:http://www.ncbi.nlm.nih.gov/projects/SNP/snp_ref.cgi?rs=10513789>]; GeneView.
Pankratz et al. "Genomewide Association Study for Susceptibility Genes Contributing to Familial Parkinson Disease. National Institutes of Health—Public Access Author Manuscript." Hum. Genet. Jan. 124(6) (2009) pp. 593-605. <doi: 10.2007/s00439-008-0582-9>.
Pierpont et al., "Genetic basis for congenital heart defects: current knowledge: a scientific statement from the American Heart Association Congenital Cardiac Defects Committee, Council on Cardiovascular disease in the Young: endorsed by the American Academy of Pediatrics" Circulation 115(23) (2007) pp. 3015-3038.
Jenkins et al., "Noninherited risk factors and congenital cardiovascular defects: a scientific statement from the American Heart

(56) References Cited

OTHER PUBLICATIONS

Association Council on Cardiovascular disease in the Young: endorsed by the American Academy of Pediatrics" Circulation 115(23) (2007) pp. 2995-3014.
Jaski et al., "Calcium upregulation by percutaneous administration of gene therapy in cardiac disease (CUPID trial), a first-in-human phase 1/2 clinical trial" J. Card. Fail 15(3) (2009) pp. 171-181.
Hauser et al., "A genome-wide scan for early-onset coronary artery disease in 438 families: the GENECARD Study" Am. J. Hum. Genet. 75(3) (2004) pp. 436-447.
Davis et al., "The overall pattern of cardiac contraction depends on a spatial gradient of myosin regulatory light chain phosphorylation" Cell 107 (2001) pp. 631-641.
Asakura et al., "Global gene expression profiling in the failing myocardium" Circ. J. 73 (2009) pp. 1568-1576.
Horne et al., "Validation study of genetic associations with coronary artery disease on chromosome 3q13-21 and potential effect modification by smoking" Ann Hum. Genet. 73(6) Nov. 2009, pp. 551-558.
Ren and Fang, "Small guanine nucleotide-binding protein Rho and myocardial function" Acta Pharmacol Sin 26(3) (2005) pp. 279-285.
Ratovitski et al., "Kalirin inhibition of inducible nitric-oxide synthase" J. Biol. Chem. 274 (1999) pp. 993-999.
Habuchi et al., "Increased risk of prostate cancer and benign hyperplasia associated with a CYP17 gene polymorphism with a gene dosage effect" Cancer Res. 60(20) (2000) pp. 5710-5713.
Berges et al., "Association of polymorphisms in CYP19A1 and CYP3A4 genes with lower urinary tract symptoms, prostate volume, uroflow and PSA in a population-based sample" World J. Urol. (2009) (Nov. 17) (epub ahead of print).
Ma et al., "Polymorphisms of fibroblast growth factor receptor 4 have association with the development of prostate cancer and benign prostatic hyperplasia and the progression of prostate cancer in a Japanese population" Int. J. Cancer 123(11) (2008) pp. 2574-2579.
Falconer et al., "Endometriosis and genetic polymorphisms" Obstet Gynecol Surv 62(9) (2007) pp. 616-628.
Nelson et al. "The program of androgen-responsive genes in neoplastic prostate epithelium" Proc. Natl. Acad. Sci., vol. 99, No. 18, Sep. 2002, pp. 11890-11895.
Catalano et al., "Mifepristone induced progesterone withdrawal reveals novel regulatory pathways in human endometrium" Mol. Hum. Reprod. 13(9) (2007) pp. 641-654.
Kettel et al., "Treatment of endometriosis with the antiprogesterone mifepristone" Fertil. Steril. 65(1) (1996) pp. 23-28.
Purcell S., "PLINK version 1.05 Software; A whole-genome association toolset; Dec. 11, 2008" published 2009, pp. 1-215. <URL:http://pngu.mgh.harvard.edu/purcell/plink>.
Nyholt et al., "Genetic basis of male pattern baldness" J. Invest. Dermatol. 121 (2003) pp. 1561-1564.
Lotufo et al., "Male pattern baldness and coronary heart disease" Arch. Intern. Med. 160 (2000) pp. 165-171.
Ellis et al., "Polymorphism of the androgen receptor gene is associated with male pattern baldness" Dermatol. 116 (2001) pp. 452-455.
Hillmer et al., "Genetic variation in the human androgen receptor gene is the major determinant of common early-onset androgenetic alopecia" Am. J. Hum. Genet. 77 (2005) pp. 140-148.
Lo et al., "Epidemiology and adverse cardiovascular risk profile of diagnosed polycystic ovary syndrome" J. Clin. Endocrinol. Metab. 91 (2006) pp. 1357-1363.
Eriksson et al., "Web-based, participant-driven studies yield novel genetic associations for common traits" PLoS Genetics, 2010.
Pritchard et al., "Linkage Disequilibrium in Humans: Models and Data" Am. J. Hum. Genet. 69 (2001) pp. 1-14.
Carlson et al., "Selecting a Maximally Informative Set of Single Nucleotide Polymorphisms for Association Analyses Using Linkage Disequilibrium" Am. J. Hum. Genet. 74 (2004) pp. 106-120.
Wigginton et al., "A note on exact tests of Hardy-Weinberg equilibrium" Am. J. Hum. Genet. 76 (2005) pp. 887-893.
Jankovic J., "Parkinson's disease: clinical features and diagnosis" J Neurol Neurosurg Psychiatr 79 (2008) pp. 368-376.
Zimprich A. et al., "Mutations in LRRK2 cause autosomal-autosomal-dominant parkinsonism with pleomorphic pathology" Neuron 44 (2004) pp. 601-607.
Kitada T. et al., "Mutations in the parkin gene cause autosomal recessive juvenile parkinsonism" Nature 392 (1998) pp. 605-608.
Valente E.M. et al., "Hereditary early-onset Parkinson's disease caused by mutations in PINK1" Science 304 (2004) pp. 1158-1160.
Bonifati V. et al., "Mutations in the DJ-1 gene associated with autosomal recessive early-onset parkinsonism" Science 299 (2003) pp. 256-259.
Ramirez A. et al., "Hereditary parkinsonism with dementia is caused by mutations in ATP13A2, encoding a lysosomal type 5 P-type ATPase" Nat Genet 38 (2006) pp. 1184-1191.
Di Fonzo A. et al., "ATP13A2 missense mutations in juvenile parkinsonism and young onset Parkinson disease" Neurology 68 (2007) pp. 1557-1562.
Tanner C.M. et al., "Parkinson disease in twins: an etiologic study" JAMA 281 (1999) pp. 341-346.
Farrer M.J., "Genetics of Parkinson disease: paradigm shifts and future prospects" Nat Rev Genet 7, (2006) pp. 306-318.
Sveinbjörnsdottir S. et al., "Familial aggregation of Parkinson's disease in Iceland" N Engl J Med 343 (2000) pp. 1765-1770.
Simon-Sanchez J. et al., "Genome-wide association study reveals genetic risk underlying Parkinson's disease" Nat Genet 41 (2009) pp. 1308-1312.
Edwards T.L. et al., "Genome-wide association study confirms SNPs in SNCA and the MAPT region as common risk factors for Parkinson disease" Ann Hum Genet 74 (2010) pp. 97-109.
Spencer C.C. et al., "Dissection of the genetics of Parkinson's disease identifies an additional association 5' of SNCA and multiple associated haplotypes at 17q21" Hum Mol Genet 20 (2011) pp. 345-353.
Hamza T.H. and Payami H., "The heritability of risk and age at onset of Parkinson's disease after accounting for known genetic risk factors" J Hum Genet 55 (2010) pp. 241-243.
Payami H. et al., "Familial aggregation of Parkinson disease: a comparative study of early-onset and late-onset disease" Arch Neurol 59 (2002) pp. 848-850.
Yang J. et al., "GCTA: A Tool for Genome-wide Complex Trait Analysis" Am J Hum Genet 88 (2011) pp. 76-82.
Aharon-Peretz J. et al., "Mutations in the glucocerebrosidase gene and Parkinson's disease in Ashkenazi Jews" N Engl J Med 351 (2004) pp. 1972-1977.
Taghibiglou C. et al., "Role of NMDA receptor-dependent activation of SREBP1 in excitotoxic and ischemic neuronal injuries" Nat Med 15(12) Dec. 2009, pp. 1399-1406.
Mosharov E.V. et al., "Interplay between cytosolic dopamine, calcium, and alpha-synuclein causes selective death of substantia nigra neurons" Neuron 62 (2009) pp. 218-229.
Li Y. et al., "Genetic evidence for ubiquitin-specific proteases USP24 and USP40 as candidate genes for late-onset Parkinson disease" Hum Mutat 27(10) (2006) pp. 1017-1023.
Wray N.R. et al., "The genetic interpretation of area under the ROC curve in genomic profiling" PLoS Genet 6 (2010) e1000864.
Alcalay R.N. et al., "Frequency of known mutations in early-onset Parkinson disease: implication for genetic counseling: the consortium on risk for early onset Parkinson disease study" Arch Neurol 67, (2010) pp. 1116-1122.
Yang J. et al., "Sporadic cases are the norm for complex disease" Eur J Hum Genet 18, (2010) pp. 1039-1043.
Falush D. et al., "Inference of population structure using multilocus genotype data:linked loci and correlated allele frequencies" Genetics 164 (2003) pp. 1567-1587.
Simon-Sanchez J. et al., "Genome-wide SNP assay reveals structural genomic variation, extended homozygosity and cell-line induced alterations in normal individuals" Hum Mol Genet (2007) 16, pp. 1-14.
Freidlin B. et al., "Trend tests for case-control studies of genetic markers: power, sample size and robustness" Hum Hered 53(2002) pp. 146-152.

(56) References Cited

OTHER PUBLICATIONS

Zou H. and Hastie T., "Regularization and variable selection via the Elastic Net" Journal of the Royal Statistical Society B 67 (2005), pp. 301-320.

Edmonds J. and Karp R., "Theoretical improvements in algorithmic efficiency for network flow problems" J ACM 19, (1972) pp. 248-264.

Orlin J.B. and Lee Y., "QuickMatch: a very fast assignment for the assignment problem" MIT Sloan School Working Paper, Mar. 1993, pp. 3547-3593.

Lunceford J.K. and Davidian M., "Stratification and weighting via the propensity score in estimation of causal treatment effects: a comparative study" Stat Med 23, (2004) pp. 2937-2960.

Janes H. and Pepe M., "Adjusting for covariate effects on classification accuracy using the covariate-adjusted receiver operating characteristic curve" Biometrika 96, Apr. 1, 2009, pp. 371-382.

Office Action dated Apr. 12, 2012 in U.S. Appl. No. 12/658,163.
Final Office Action dated Nov. 20, 2012 in U.S. Appl. No. 12/658,163.
Office Action dated May 8, 2014 in U.S. Appl. No. 12/658,163.
Final Office Action dated Nov. 6, 2014 in U.S. Appl. No. 12/658,163.
Office Action dated Apr. 1, 2015 in U.S. Appl. No. 12/658,163.
Final Office Action dated Nov. 27, 2015 in U.S. Appl. No. 12/658,163.
Office Action dated Jul. 11, 2016 in U.S. Appl. No. 12/658,163.
Office Action dated Dec. 24, 2014 in U.S. Appl. No. 13/304,091.
Final Office Action dated Jul. 10, 2015 in U.S. Appl. No. 13/304,091.

1000 Genomes Project Consortium, et al., "A Global Reference for Human Genetic Variation" Nature, vol. 526, Oct. 1, 2015 pp. 68-74.

23andMe African Genetics Project [Webpage] "The African Genetics Project" 2016, pp. 1-7. <URL:https://www.23andme.com/africa-project/>.

ADA (American Diabetes Association) "Economic Costs of Diabetes in the U.S. in 2017" Diabetes Care (May 2018) vol. 41, pp. 917-928.

Aekplakorn, W. et al., "A risk score for predicting incident diabetes in the Thai population" Diabetes Care 2006;29:1872-1877.

Almgren, et al., "Heritability and familiality of type 2 diabetes and related quantitative traits in the Botnia Study" Diabetologia 54 (2011) pp. 2811-2819.

Alssema, M. et al. "The Evaluation of Screening and Early Detection Strategies for Type 2 Diabetes and Impaired Glucose Tolerance (DETECT-2) update of the Finnish diabetes risk score for prediction of incident type 2 diabetes" Diabetologia 2011;54:1004-12.

Astrup, A. et al., "Safety, tolerability and sustained weight loss over 2 years with the once-daily human GLP-1 analog, liraglutide" International Journal of Obesity, vol. 36, (2012) pp. 843-854.

Balkau, B. et al. "Predicting diabetes: clinical, biological, and genetic approaches: data from the Epidemiological Study on the Insulin Resistance Syndrome (DESIR)" Diabetes Care 31:10 (2008) pp. 2056-2061.

Bickel, J.E., "Some Comparisons among Quadratic, Spherical, and Logarithmic Scoring Rules" Decision Analysis, vol. 4, No. 2, Jun. 2007, pp. 49-65.

Boyle, J.P. et al., "Projection of the year 2050 burden of diabetes in the US adult population: dynamic modeling of incidence, mortality, and prediabetes prevalence" Population Health Metrics, 8:29 (2010) pp. 1-12.

Bozorgmanesh, M. et al. "A simple risk score effectively predicted type 2 diabetes in Iranian adult population: population-based cohort study" Eur J Public Health 21:5 (2011) pp. 554-559.

CDC and National Center for Health Statistics, [Webpage] "Underlying cause of death 1999-2016 on CDC WONDER Online database, released Dec. 2017. Data are from the Multiple Cause of Death Files, 1999-2016, as compiled from data provided by the 57 vital statistics jurisdictions through the Vital Statistics Cooperative Program" (2017) 1 page. <URL:http://wonder.cdc.gov/ucd-icd10.html>.

Chang, C.C. et al., "Second-generation PLINK: rising to the challenge of larger and richer datasets" Gigascience 4:7 (2015) pp. 1-16. [doi:10.1186/s13742-015-0047-8].

Chen, et al., "AUSDRISK: an Australian Type 2 Diabetes Risk Assessment Tool based on demographic, lifestyle and simple anthropometric measures" MJA vol. 192, No. 4, Feb. 15, 2010, pp. 197-202.

Chiasson, J.L. et al., "Acarbose for prevention of type 2 diabetes mellitus: the STOP-NIDDM randomised trial" Lancet 359, (2002) pp. 2072-2077.

Chien, K. et al. "A prediction model for type 2 diabetes risk among Chinese people" Diabetologia 2009;52, pp. 443-50.

Coram, M.A., et al., "Leveraging Multi-ethnic Evidence for Risk Assessment of Quantitative Traits in Minority Populations" Am. J. Hum. Genet. 101, (2017) pp. 218-226.

Dall, T.M. et al., "The economic burden of elevated blood glucose levels in 2012: diagnosed and undiagnosed diabetes, gestational diabetes mellitus, and prediabetes" Diabetes Care vol. 37, Dec. 2014, pp. 3172-3179. <doi:10.2337/dc14-1036>.

Dawid, P., "Present Position and Potential Developments: Some Personal Views: Statistical Theory: The Prequential Approach" Journal of the Royal Statistical Society. Series A (General) vol. 147, No. 2, (1984) pp. 278-292.

Durand, et al., "Ancestry Composition: A Novel, Efficient Pipeline for Ancestry Deconvolution" 23andMe White paper, Oct. 17, 2014, pp. 23-16.

Expert Panel, "Obesity in Adults" NIH Publication No. 98-4083, Sep. 1998, National Institute of Health, pp. 1-228.

Fuchsberger, C. et al., "minimac2: faster genotype imputation" Bioinformatics, 31(5), 2015, pp. 782-784.

Furlotte, N. et al., "White paper 23-12—Estimating Complex Phenotype Prevalence Using Predictive Model" 23andMe White paper 23-12 (2015).

Gail, M.H. et al., "Projecting individualized probabilities of developing breast cancer for white females who are being examined annually" J. Natl. Cancer Inst., vol. 81, No. 24, Dec. 20, 1989, pp. 1879-1886.

Gneiting, T. et al., "Probabilistic forecasts, calibration and sharpness" Hal-00363242 (2007) pp. 1-28. <URL:https://hal.archives-ouvertes.fr/hal-00363242>.

Greenhalgh, T. et al. "Protocol—realist and meta-narrative evidence synthesis: Evolving Standards (RAMESES)" BMC Medical Research Methodology 11:115 (2011) pp. 1-10.

Guerrero-Romero, et al., "Validation of an instrument for screening cases of type 2 diabetes and monitoring at-risk individuals in Mexico" Rev. Panam. Salud Publica 27(3), (2010) pp. 181-186.

Hamza T.H. et al., "Common genetic variation in the HLA region is associated with late-onset sporadic Parkinson's disease" Nat Genet 42 (2010) pp. 781-785.

Hindorff L.A. et al., "Potential etiologic and functional implications of genome-wide association loci for human diseases and traits" Proc Natl Acad Sci USA 106, (2009) pp. 9362-9367.

Hippisley-Cox, J. et al. "Predicting risk of type 2 diabetes in England and Wales: prospective derivation and validation of QDScore" BMJ 2009;338:b880.

Hu, Y. et al. "GWAS of 89,283 Individuals Identifies Genetic Variants Associated with Self-Reporting of Being a Morning Person" Nature Communications 7, (2016) pp. 1-9. <doi:10.1038/ncomms10448>.

Ioannidis J.P. et al., "Assessment of cumulative evidence on genetic associations: interim guidelines" Int J Epidemiol 37 (2008) pp. 120-132.

Iribarren, C., et al. "Weighted Multi-marker Genetic Risk Scores for Incident Coronary Heart Disease among Individuals of African, Latino and East-Asian Ancestry" Scientific Reports 8:6853, May 1, 2018, pp. 1-13.

Kahn, H.S. et al. "Two risk-scoring systems for predicting incident diabetes mellitus in US adults age 45 to 64 years" Ann Intern Med 2009;150, pp. 741-751.

Katzmarzyk, et al., "Adiposity, physical fitness and incident diabetes: the physical activity longitudinal study" Diabetologia 50, (2007) pp. 538-544.

Kavvas, et al., "A biochemically-interpretable machine learning classifier for microbial GWAS" Nature Communications 11 (2020) pp. 1-11. <URL:https://doi.org/10.1038/s41467-02016310-9>.

(56) References Cited

OTHER PUBLICATIONS

Khera, A.V. et al., "Genome-wide polygenic scores for common diseases identify individuals with risk equivalent to mongenic mutations" Nature Genetics, vol. 50, Sep. 2018, pp. 1219-1224.
Knowler, et al., "Reduction in the incidence of type 2 diabetes with lifestyle intervention or metformin" N. Engl. J. Med. 346, (2002) pp. 393-403.
Läll, K. et al., "Personalized risk prediction for type 2 diabetes: the potential of genetic risk scores" Genet. Med., vol. 19, No. 3, Mar. 2017, pp. 322-329.
Lean, M.E., et al. "Primary care-led weight management for remission of type 2 diabetes (DiRECT): an open-label, cluster-randomised trial" Lancet 391, (2018) pp. 541-551.
Lello, L. et al., "Accurate Genomic Prediction of Human Height" Genetics, vol. 210, Oct. 2018, pp. 477-497.
Lily, M. et al., "Treating prediabetes with metformin: systematic review and meta-analysis" Can. Fam. Physician 55, Apr. 2009, pp. 363-369.
Lindstrom, J. et al., "The diabetes risk score: a practical tool to predict type 2 diabetes risk" Diabetes Care 26:3 (2003) pp. 725-731.
Lobo, et al., "AUC: a misleading measure of the performance of predictive distribution models" Global Ecology and Biogeography, (2007) pp. 1-7. <doi:10.1111/j.1466-8238.2007.00358.x>.
Loh, et al., "Reference-based phasing using the Haplotype Reference Consortium panel" Nat. Genet. 48:11, Nov. 2016, pp. 1443-1448.
Mann, D.M., et al. "Comparative validity of 3 diabetes mellitus risk prediction scoring models in a multiethnic US cohort: the Multi-Ethnic Study of Atherosclerosis" Am J Epidemiol 171:9, (2010) pp. 980-988.
Márquez-Luna, et al., "Multiethnic polygenic risk scores improve risk prediction in diverse populations" Genet. Epidemiol. 41, (2017) pp. 811-823.
Martin, A.R. et al., "Human Demographic History Impacts Genetic Risk Prediction across Diverse Populations" Am. J. Hum. Genet. 100, (2017) pp. 635-649.
Mavaddat, N. et al., "Prediction of breast cancer risk based on profiling with common genetic variants" J. Natl. Cancer Inst. 107:5 (2015) pp. 1-15.
Mehrabi, Y. et al. "Prediction of diabetes using logic regression" Iran J Endocrinol Metab 12:1, May 2010, pp. 16-24.
Meigs, et al., "Genotype score in addition to common risk factors for prediction of type 2 diabetes" N. Engl. J. Med. 2008;359:2208-9.
Mejia-Guevara, et al., "Association of a Genetic Risk Score with Body Mass Index Across Different Birth Cohorts" JAMA Jul. 5, 2016; 316(1), pp. 63-69.
Multhaup, M. et al., "White paper 23-17, The science behind 23andMe's Genetic Weight report" 23andMe White paper 23-17 (2017).
Multhaup, M. et al., "White paper 23-19, The science behind 23andMe's Type 2 Diabetes report" 23andMe White paper 23-19 (2019).
Nichols W.C. et al., "Mutations in GBA are associated with familial Parkinson disease susceptibility and age at onset" Neurology 72 (2009) pp. 310-316.
Noble, et al., "Risk models and scores for type 2 diabetes: systematic review" BMJ 343, d7163, Nov. 28, 2011, pp. 1-31.
Pandya, a. et al., "Cost-effectiveness of 10-Year Risk Thresholds for Initiation of Statin Therapy for Primary Prevention of Cardiovascular Disease" JAMA. 314(2) Jul. 14, 2015, pp. 142-150.
Park, K.S. "The search for genetic risk factors of type 2 diabetes mellitus" Diabetes Metab J 2011;35, pp. 12-22.
Pruim R.J. et al., "LocusZoom: regional visualization of genome-wide association scan results" Bioinformatics 26 (2010) pp. 2336-2337.
Rahman, M. et al. "A simple risk score identifies individuals at high risk of developing type 2 diabetes: a prospective cohort study" Fam Pract 2008;25, pp. 191-196.
Ranjan, R. "Combining and Evaluating Probabilistic Forecasts" Dissertation, University of Washington (2009) pp. 1-102.
Rathmann, W. et al. "Prediction models for incident type 2 diabetes mellitus in the older population: KORA S4/F4 cohort study" Diabet. Med. 27 (2010) pp. 1116-1123.
Rathmann, W. et al., "Development of a type 2 diabetes risk model from a panel of serum biomarkers from the Inter99 cohort" Diabetes Care, Feb. 2010, vol. 33, No. 2, p. 1.
Rosella, L.C. et al., "A population-based risk algorithm for the development of diabetes: development and validation of the Diabetes Population Risk Tool (DPoRT)" J Epidemiol Community Health 65 (2011) pp. 613-620.
Saad M. et al., "Genome-wide association study confirms BST1 and suggests a locus on 12q24 as the risk loci for Parkinson's disease in the European population" Hum Mol Genet 20 (2011) pp. 615-627.
Saslow, D. et al., "American Cancer Society Guidelines for Breast Screening with MRI as an Adjunct to Mammography" CA Cancer J. Clin. 57, Mar./Apr. 2007, pp. 75-89.
Satake W. et al., "Genome-wide association study identifies common variants at four loci as genetic risk factors for Parkinson's disease" Nat Genet 41 (2009) pp. 1303-1307.
Sato, D. et al., [Webpage] "Continuous Delivery for Machine Learning" Sep. 19, 2019, pp. 1-33. [retrieved on May 7, 2020] <URL:http://www.martinfowler.com/articles/cd4mi.html>.
Schulze, M.B., et al. "An accurate risk score based on anthropometric, dietary, and lifestyle factors to predict the development of type 2 diabetes" Diabetes Care 30:Mar. 3, 2007, pp. 510-515.
Schulze, M.B., et al. "Use of multiple metabolic and genetic markers to improve the prediction of type 2 diabetes: the EPIC-Potsdam Study" Diabetes Care 32: 11, Nov. 2009, pp. 2116-2119.
Scott, R.A., et al., "An Expanded Genome-Wide Association Study of Type 2 Diabetes in Europeans" Diabetes, vol. 66, Nov. 2017, pp. 2888-2902.
Sculley, D. et al. "Hidden Technical Debt in Machine Learning Systems" Google, Inc. (2015) pp. 1-9.
Sheikh, et al., "The predictive effect of body mass index on Type 2 diabetes in the Norwegian women and cancer study" Lipids in Health Disease, 13:164 (2014) pp. 1-8.
Spencer C. et al., "Dissection of the genetics of Parkinson's disease identifies an additional association 5' of SNCA and multiple associated haplotypes at 17q21" Hum Mol Genet 20 (2011) pp. 345-353.
Stern, et al., "Validation of prediction of diabetes by the Archimedes model and comparison with other predicting models" Diabetes Care 31:8, Aug. 2008, pp. 1670-1671.
Steyerberg, E. et al., "Assessing the performance of prediction models: a framework for some traditional and novel measures" Epidemiology. Jan. 2010; 21(1): pp. 128-138. <doi:10.1097/EDE. 0b013e3181c30fb2>.
Sun, F. et al., "An accurate risk score for estimation 5-year risk of type 2 diabetes based on a health screening population in Taiwan" Diabetes Res Clin Pract 2009;85, pp. 228-234.
Tabak, et al., "Prediabetes: a high-risk state for diabetes development" Lancet, 379(9833) Jun. 16, 2012, pp. 2279-2290.
Talmud, P.J. et al., "Utility of genetic and non-genetic risk factors in prediction of type 2 diabetes: Whitehall II prospective cohort study" BMJ 2010;340:b4838.
Tishkoff, S.A. et al., "The genetic structure and history of Africans and African Americans" Science 324(5930), May 22, 2009, pp. 1035-1044.
Tuomilehto, J. et al., "Prevention of Type 2 diabetes mellitus by changes in lifestyle among subjects with impaired glucose tolerance" N. Engl. J. Med. 344:18, May 3, 2001, pp. 1343-1350.
Trial Investigators, et al., "DREAM (Diabetes Reduction Assessment with ramipril and rosilglitazone Medication)—Effect of rosiglitazone on the frequency of diabetes in patients with impaired glucose tolerance or impaired fasting glucose: a randomised controlled trial," Lancet 368, (2006) pp. 1096-1105.
UK10K Consortium et al., "The UK10K project identifies rare variants in health and disease" Nature 526, Oct. 1, 2015, pp. 82-90.
Urdea, M. et al. "Validation of a multimarker model for assessing risk of type 2 diabetes from a five-year prospective study of 6784 Danish people (Inter 99)" J Diabetes Sci Technol 3, 2009, pp. 748-755.

(56) References Cited

OTHER PUBLICATIONS

Vilhjalmsson, B.J. et al. "Modeling Linkage Disequilibrium Increases Accuracy of Polygenic Risk Scores" Am. J. Hum. Genet. 97, Oct. 1, 2015, pp. 576-592.
Wannamethee, S.G. et al. "Metabolic syndrome vs Framingham Risk Score for prediction of coronary heart disease, stroke, and type 2 diabetes mellitus" Arch Intern Med 2005;165, pp. 2644-2650.
Wareham, N.J. et al. "Risk scores for predicting type 2 diabetes: comparing axes and spades" Diabetologia 54, (2011) pp. 994-995.
WHO Expert Consultation, "Appropriate body-mass index for Asian populations and its implications for policy and intervention strategies" Lancet 363, (2004) pp. 157-163.
WHO International Association for the Study of Obesity, International Obesity Task Force "The Asia-Pacific perspective: Redefining Obesity and its Treatment" Sydney, Australia, Health Communications 2000, pp. 1-56.
WHO Technical Report Series 894, "Obesity: preventing and managing the global epidemic" WHO Technical Report Series 894 (2000) pp. 1-253.
U.S. Appl. No. 12/658,163, filed Feb. 2, 2010, Polcari, et al.
U.S. Appl. No. 13/304,091, filed Nov. 23, 2011, Naughton, et al.

\* cited by examiner

| Member ID | Genetic Information | | Family History Information | | Environmental Information | | Has PD? |
|---|---|---|---|---|---|---|---|
| | SNP rs12778775 risk allele | ... | Mother has PD? | ... | Exposed to pesticides at work? | | |
| 0001 | yes | ... | yes | ... | no | ... | yes |
| 0002 | no | ... | no | ... | yes | ... | yes |
| ... | ... | ... | ... | ... | ... | ... | ... |
| 2999 | no | ... | no | ... | yes | ... | no |
| 3000 | yes | ... | no | ... | no | ... | no |
| ... | | | | | | | |
| 4000 | no | ... | no | ... | no | ... | yes |
| ... | ... | ... | ... | ... | ... | ... | ... |

FIG. 4

DATABASE AND DATA PROCESSING SYSTEM FOR USE WITH A NETWORK-BASED PERSONAL GENETICS SERVICES PLATFORM

INCORPORATION BY REFERENCE

An Application Data Sheet is filed concurrently with this specification as part of the present application. Each application that the present application claims benefit of or priority to as identified in the concurrently filed Application Data Sheet is incorporated by reference herein in its entirety and for all purposes.

BACKGROUND OF THE INVENTION

DNA sequencing technology has seen dramatic improvements in the past few years and the cost of sequencing has been declining rapidly. It is easier than ever to perform genetic testing to determine whether an individual has a particular genetic marker proven to be linked to certain disease conditions. Genetic tests are available to check for such deleterious mutations. The mere presence of mutation in a genetic marker, however, is typically only one of the many factors that are related to the disease risk. The complexity of how a variety of different factors may contribute to the disease risk makes it difficult to accurately predict the risk level an individual faces.

BRIEF DESCRIPTION OF THE DRAWINGS

Various embodiments of the invention are disclosed in the following detailed description and the accompanying drawings.

FIG. 4 is a diagram illustrating an embodiment of a member information table used to train and validate the model.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Figure 1:
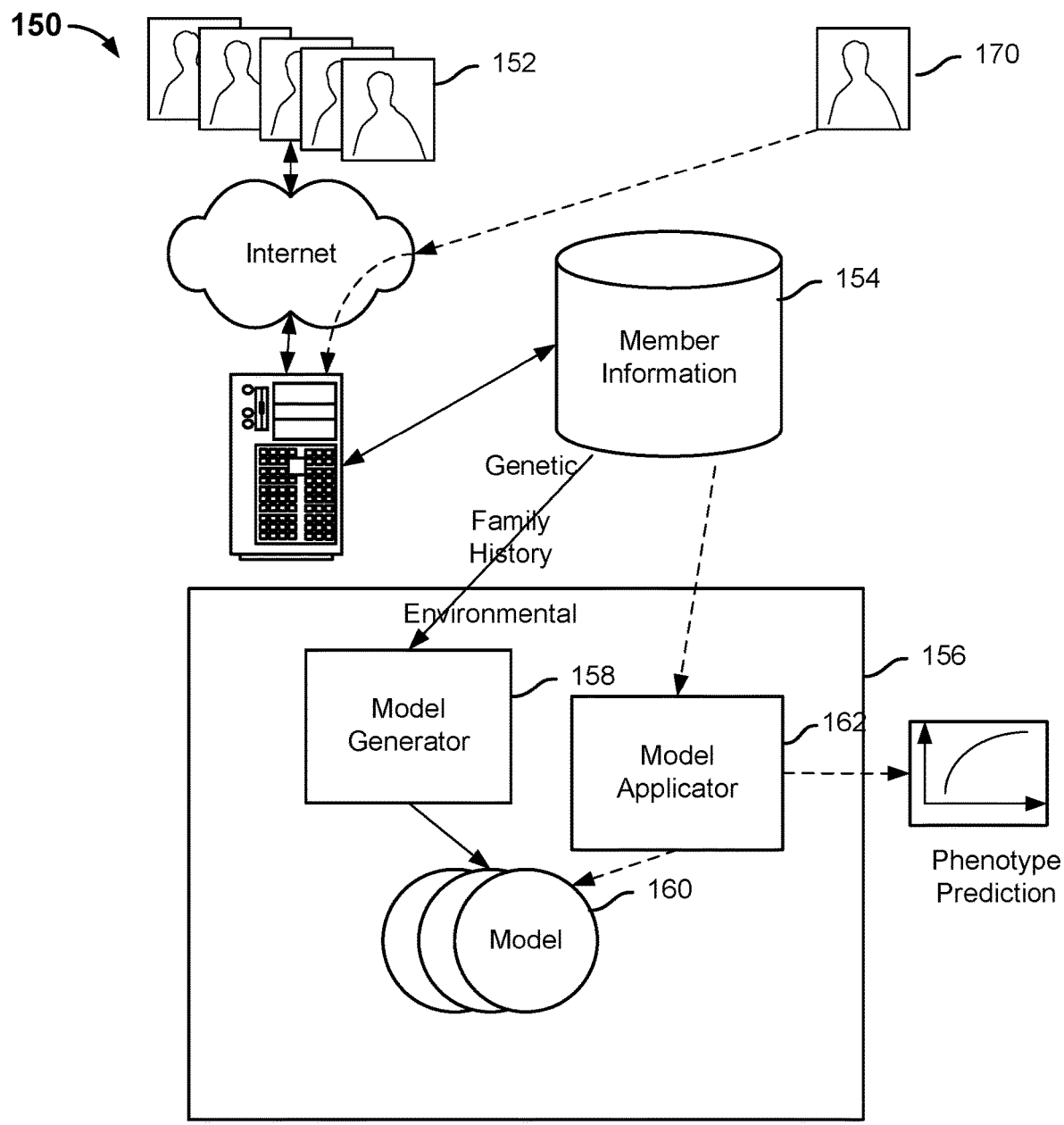
FIG. 1 is a system diagram illustrating an embodiment of an automated phenotype prediction system.

FIG. 1 is a system diagram illustrating an embodiment of an automated phenotype prediction system. In this example, system 150 includes a personal genetics services platform (such as the platform implemented by 23andMe, Inc.) used to collect information from its members. Certain members 152 of the service log on to the website operated by the personal genetics service provider to fill out survey information about their family history (e.g., disease history of relatives), environment (e.g., smoking habits, diet, exposure to toxins, etc.), as well as phenotype data (e.g., other concurrent diseases/conditions). The family history and environmental information is stored in one or more databases 154. DNA samples (e.g., saliva, blood, etc.) are collected from the members and analyzed using DNA microarray or other appropriate techniques. The genetic information is also stored in a database that may be the same as or separate from database 154. In various embodiments, the genetic information includes gene sequences, single-nucleotide polymorphisms (SNPs), and/or other representations of the members' genes.

A phenotype prediction engine 156 is used to predict a phenotype given certain information about an individual. Phenotypes that can be predicted by the prediction engine include disease as well as non-disease related traits, such as height, weight, body mass index (BMI), cholesterol levels, etc. The types of predictions include but are not limited to the probability of a disease occurring over the course of an individual's lifetime, the probability of a disease occurring within a specific time frame, the probability that the individual currently has the disease, estimates of the value of a quantitative measurement, or estimates of the distribution of likely measurements.

In this example, the engine includes a model generator 158 that is configured to obtain genetic, family history, and environmental information about members from the database and determine models 160 for predicting the various phenotypes. In some embodiments, the models are stored in a database or other appropriate storage location. Details of how to determine the models in some embodiments are described more fully below.

Once the models are determined, a member 170 (who may or may not be a part of the cohort used to form the models) can initiate a request via the web interface to make a prediction about a certain phenotype (such as a particular disease). The request is sent, in this case via the webserver, to the phenotype prediction engine, which invokes a model applicator 162. The model applicator retrieves genetic, family history, and environmental information about the requesting member from the database, applies the information to the appropriate model, and outputs a phenotype prediction.

The phenotype prediction engine, its model generator and model applicator described above can be implemented as software components executing on one or more general purpose processors, as hardware such as programmable logic devices and/or Application Specific Integrated Circuits designed to perform certain functions or a combination thereof. In some embodiments, these modules can be embodied by a form of software products which can be stored in a nonvolatile storage medium (such as optical disk, flash storage device, mobile hard disk, etc.), including a number of instructions for making a computer device (such as personal computers, servers, network equipment, etc.) implement the methods described in the embodiments of the present invention. The modules may be implemented on a single device or distributed across multiple devices. The functions of the modules may be merged into one another or further split into multiple sub-modules.

Figure 2:
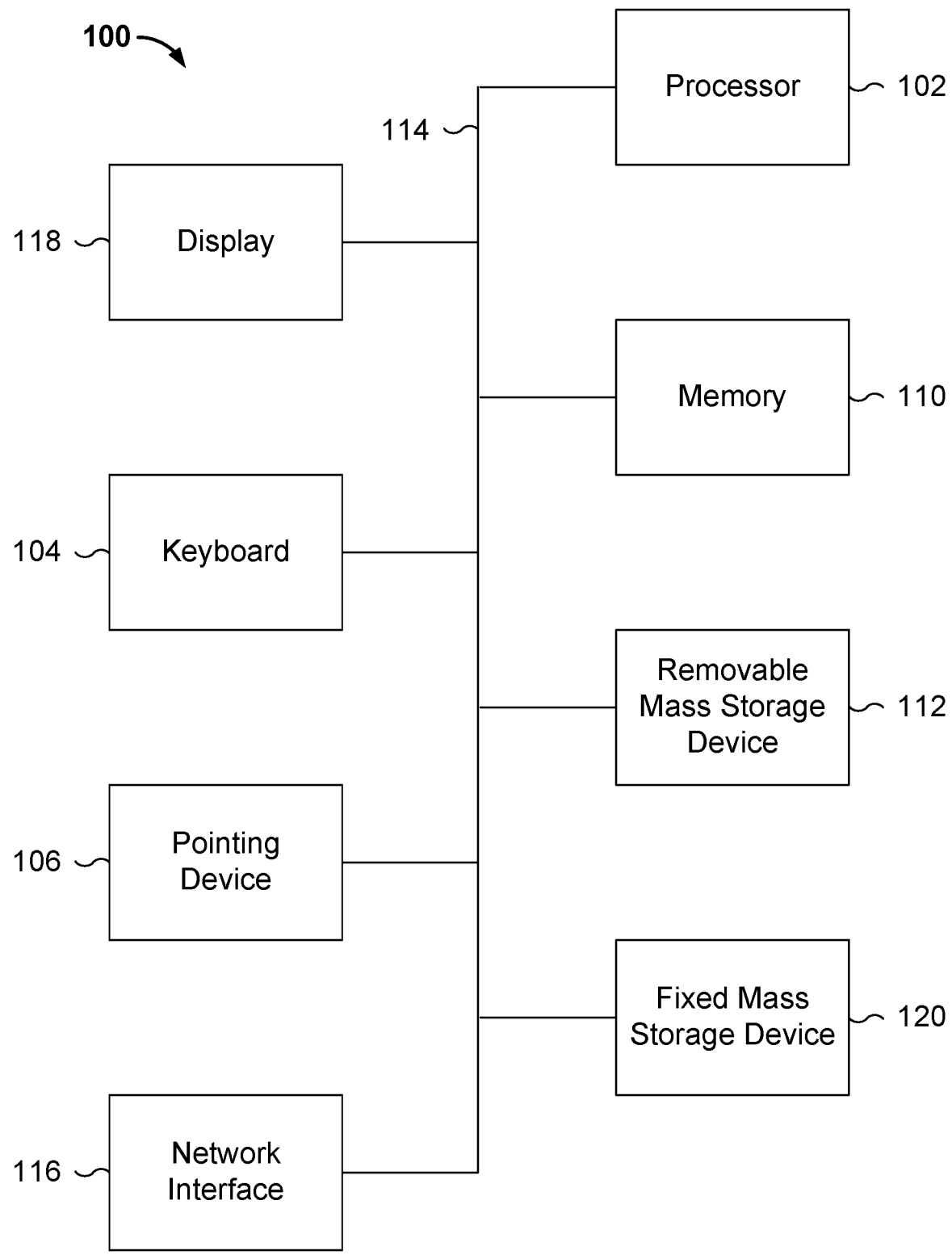
FIG. 2 is a functional diagram illustrating a programmed computer system for making phenotype predictions in accordance with some embodiments.

FIG. 2 is a functional diagram illustrating a programmed computer system for making phenotype predictions in accordance with some embodiments. As will be apparent, other computer system architectures and configurations can be used to perform phenotype predictions. Computer system 100, which includes various subsystems as described below, includes at least one microprocessor subsystem (also referred to as a processor or a central processing unit (CPU)) 102. For example, processor 102 can be implemented by a single-chip processor or by multiple processors. In some embodiments, processor 102 is a general purpose digital processor that controls the operation of the computer system 100. Using instructions retrieved from memory 110, the processor 102 controls the reception and manipulation of input data, and the output and display of data on output devices (e.g., display 118). In some embodiments, processor 102 includes and/or is used to implement model generator 158 and model applicator 162 described above, and/or executes/performs the processes described below with respect to FIG. 3.

Processor 102 is coupled bi-directionally with memory 110, which can include a first primary storage, typically a random access memory (RAM), and a second primary storage area, typically a read-only memory (ROM). As is well known in the art, primary storage can be used as a general storage area and as scratch-pad memory, and can also be used to store input data and processed data. Primary storage can also store programming instructions and data, in the form of data objects and text objects, in addition to other data and instructions for processes operating on processor 102. Also as is well known in the art, primary storage typically includes basic operating instructions, program code, data, and objects used by the processor 102 to perform its functions (e.g., programmed instructions). For example, memory 110 can include any suitable computer readable storage media, described below, depending on whether, for example, data access needs to be bi-directional or unidirectional. For example, processor 102 can also directly and very rapidly retrieve and store frequently needed data in a cache memory (not shown).

A removable mass storage device 112 provides additional data storage capacity for the computer system 100, and is coupled either bi-directionally (read/write) or uni-directionally (read only) to processor 102. For example, storage 112 can also include computer readable media such as magnetic tape, flash memory, PC-CARDS, portable mass storage devices, holographic storage devices, and other storage devices. A fixed mass storage device 120 can also, for example, provide additional data storage capacity. The most common example of mass storage 120 is a hard disk drive. Mass storage 112 and 120 generally store additional programming instructions, data, and the like that typically are not in active use by the processor 102. It will be appreciated that the information retained within mass storage 112 and 120 can be incorporated, if needed, in standard fashion as part of memory 110 (e.g., RAM) as virtual memory.

In addition to providing processor 102 access to storage subsystems, bus 114 can be used to provide access to other subsystems and devices. As shown, these can include a display monitor 118, a network interface 116, a keyboard 104, and a pointing device 106, as well as an auxiliary input/output device interface, a sound card, speakers, and other subsystems as needed. For example, the pointing device 106 can be a mouse, stylus, track ball, or tablet, and is useful for interacting with a graphical user interface.

The network interface 116 allows processor 102 to be coupled to another computer, computer network, or telecommunications network using a network connection as shown. For example, through the network interface 116, the processor 102 can receive information (e.g., data objects or program instructions) from another network or output information to another network in the course of performing method/process steps. Information, often represented as a sequence of instructions to be executed on a processor, can be received from and outputted to another network. An interface card or similar device and appropriate software implemented by (e.g., executed/performed on) processor 102 can be used to connect the computer system 100 to an external network and transfer data according to standard protocols. For example, various process embodiments disclosed herein can be executed on processor 102, or can be performed across a network such as the Internet, intranet networks, or local area networks, in conjunction with a remote processor that shares a portion of the processing. Additional mass storage devices (not shown) can also be connected to processor 102 through network interface 116.

An auxiliary I/O device interface (not shown) can be used in conjunction with computer system 100. The auxiliary I/O device interface can include general and customized interfaces that allow the processor 102 to send and, more typically, receive data from other devices such as microphones, touch-sensitive displays, transducer card readers, tape readers, voice or handwriting recognizers, biometrics readers, cameras, portable mass storage devices, and other computers.

In addition, various embodiments disclosed herein further relate to computer storage products with a computer readable medium that includes program code for performing various computer-implemented operations. The computer readable medium is any data storage device that can store data which can thereafter be read by a computer system. Examples of computer readable media include, but are not limited to, all the media mentioned above: magnetic media such as hard disks, floppy disks, and magnetic tape; optical media such as CD-ROM disks; magneto-optical media such as optical disks; and specially configured hardware devices such as application-specific integrated circuits (ASICs), programmable logic devices (PLDs), and ROM and RAM devices. Examples of program code include both machine code, as produced, for example, by a compiler, or files containing higher level code (e.g., script) that can be executed using an interpreter.

The computer system shown in FIG. 2 is but an example of a computer system suitable for use with the various embodiments disclosed herein. Other computer systems suitable for such use can include additional or fewer subsystems. In addition, bus 114 is illustrative of any interconnection scheme serving to link the subsystems. Other computer architectures having different configurations of subsystems can also be utilized.

Figure 3:
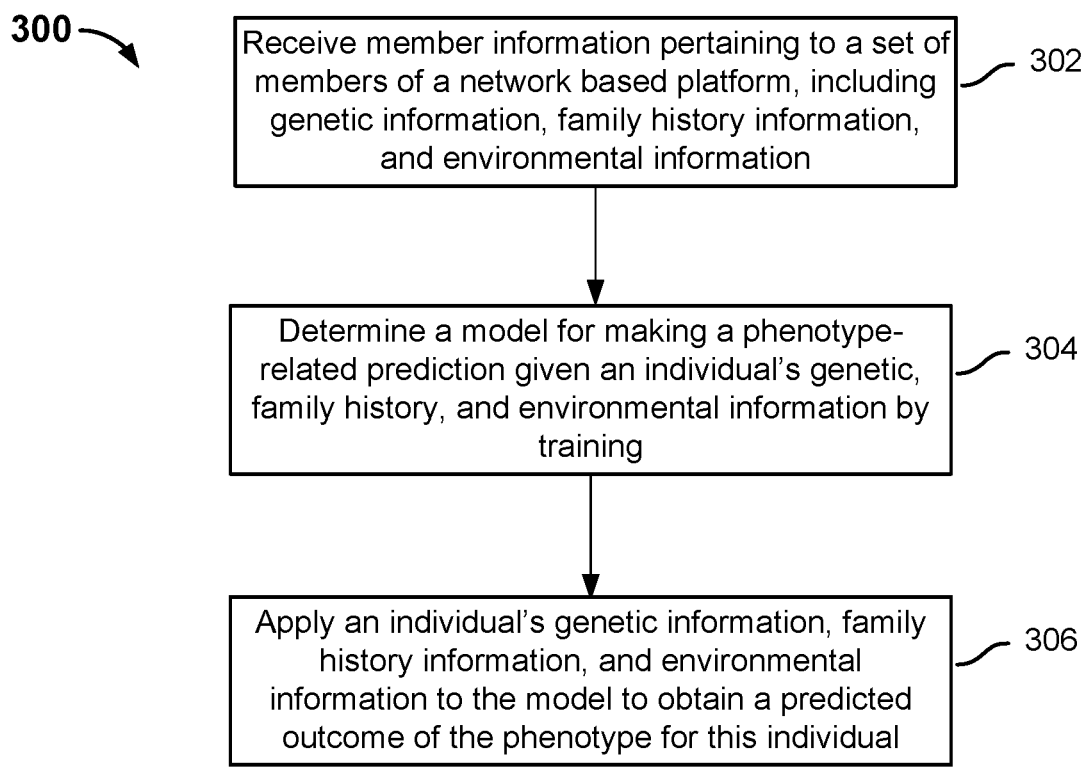
FIG. 3 is a flowchart illustrating an embodiment of a process for phenotype prediction.

FIG. 3 is a flowchart illustrating an embodiment of a process for phenotype prediction. Process 300 may be implemented on a system such as 100. The process uses the information of a significant number of members to build and optionally validate a model for phenotype prediction.

At 302, member information pertaining to a plurality of members of a network-based platform is received. One example of a network-based platform is the Personal Genome Service® operated by 23andMe. In some embodiments, the member information is retrieved from one or more databases. The member information includes genetic information, family history information, and environmental information of the members.

In some embodiments, the family history information (e.g., a relative has a particular disease and the age of diagnosis) and the environmental information (e.g., exposure to toxic substances) are provided by the members, who fill out online questionnaires/surveys for themselves. In some embodiments, some of the family history information and environmental information is optionally provided by other members. For example, some online platforms allow members to identify their relatives who are also members of the online platforms, and make connection with each other to form family trees. Members may authorize other connected relatives to edit the family history information and/or environmental information. For example, two members of the network-based platform may be cousins. They may authorize each other to fill out parts of their collective family history, such as the medical history of grandparents, uncles, aunts, other cousins, etc. The genetic information, family history information, and/or environmental information may also be retrieved from one or more external databases such as patient medical records.

At 304, a model is determined for making a phenotype-related prediction given an individual's genetic, family history, and environmental information. In some embodiments, modeling techniques (e.g., machine learning techniques such as regularized logistic regression, decision tree, support vector machine, etc.) are applied to all or some of the member information to train a model for predicting the likelihood associated with a phenotype such as a disease as well as the likelihood of having a non-disease related genotype such as eye color, height, etc. In some embodiments, the models are derived based on parameters published in scientific literature and/or a combination of literature and learned parameters. As will be described in greater detail below, in some embodiments, the model will account for, among other things, genetic inheritance and any known relationships between genetic information and the phenotype.

At 306, an individual's genetic information, family history information, and environmental information is applied to the model to obtain a predicted outcome of the phenotype for this individual. In some embodiments, the predicted outcome is age dependent. In other words, the predicted outcome indicates how likely the individual may have a particular disease by a certain age/age range.

An embodiment of a process for determining a model is described in an example below. For purposes of illustration, the phenotype of interest in the example is Parkinson's disease (PD), although models may be derived for risk prediction of many other phenotypes. A technique for identifying polymorphisms associated with PD is disclosed in co-pending U.S. patent application Ser. No. 12/956,525 entitled Polymorphisms Associated with Parkinson's Disease, filed Nov. 30, 2010, which is incorporated herein by reference for all purposes in its entirety. The same technique may be used for determining models for predicting other phenotypes.

FIG. 4 is a diagram illustrating an embodiment of a member information table used to train and validate the model. In this example, member information with respect to Parkinson's disease is kept in the table, where each row corresponds to the information of a member, and each column corresponds to a particular piece of information. Multiple columns are grouped to correspond to genetic information, family history information, environmental information, etc. The genetic information includes whether the member possesses risk alleles in SNPs found to be independently associated with PD; the family history information includes answers to survey questions such as whether the mother or father has PD; and the environmental information includes answers to survey questions such as whether the member has had pesticide exposure at work. In addition, the table stores the members' PD status and optionally personal information, such as age, geographical location, etc.

In some embodiments, a logistic regression technique is used to determine the model. In this example, a subset of the rows (e.g., member data for members 1-3000) is selected as training data and the remaining rows (e.g., member data for members 3001-4000) are used for validation.

In one example where logistic regression is performed, for each row of the table, the genetic and environmental information is encoded as a multidimensional vector. Many possible encoding techniques exist. One example of a specific encoding technique is to include the number of copies of risk alleles for each SNP (0, 1, or 2) as separate entries in the vector, the presence or absence of PD in any relative (0=no, 1=yes), and the presence or absence of various environmental factors (0=no, 1=yes, per environmental factor); we refer to each of the elements of the vector as "features." For notational convenience, we denote the multidimensional vector for the i-th row of the table as $x^{(i)}=(x_{i,1}, x_{i,2}, \ldots, x_{i,n})$. Here, n represents the number of encoded features, and $x_{i,j}$ represents the j-th encoded feature for the i-th example. Let m denote the number of examples in the training set, and let $y=(y^{(1)}, y^{(2)}, \ldots, y^{(m)})$ denote an encoding of the phenotypes for each individual in the training set ($y^{(i)}=1$ indicates that the i-th individual reported developing the disease, whereas $y^{(i)}=0$ indicates that the i-th individual did not report developing the disease).

In the logistic regression example, we consider a model of the form $$P(y=1|x;w,b)=1/(1+\exp(-w^T x-b)) \quad (1).$$

Here, x corresponds to an n-dimensional vector of encoded features, and y is the encoded phenotype. The parameters of the model include b (a real-valued intercept term) and $w=(w_1, w_2, \ldots, w_n)$ (an n-dimensional vector of real-values). The notation $w^T x$ is taken to mean the dot product of the vectors w and x (i.e., $\Sigma_{j=1,\ldots,n} w_j x_j$). The exp( ) operator refers to exponentiation base e. As specified above, for any vector x, the logistic regression model outputs a value between 0 and 1 indicating the probability that an individual with encoded features x will report having developed the phenotype such as a disease (i.e., y=1).

In the logistic regression example, the parameters of the model (w and b) are chosen to maximize the logarithm (base e) of the regularized likelihood of the data; this quantity, known as the regularized log-likelihood, is specified as follows:

$$L(w,b)=\Sigma_{i=1,\ldots,m} \log P(y^{(i)}|x^{(i)};w,b)-0.5C\, w^T w \quad (2).$$

Here, C is a real-valued hyperparameter that is chosen via cross-validation (as described below). The first term of the objective function is a log-likelihood term that ensures that the parameters are a good fit to the training data. The second term of the objective (i.e., $0.5\, w^T w$) is a regularization penalty that helps to ensure that the model does not overfit. The hyperparameter C controls the trade-off between the two terms, so as to ensure that the predictions made by the learned model will generalize properly on unseen data.

In the logistic regression example, a cross-validation procedure is used to select the value of the hyperparameter C. In this procedure, we fit the parameters of the model (w and b) by maximizing the objective function specified in equation (1) for multiple values of C (e.g., . . . ⅛, ¼, ½, 1, 2, 4, 8, . . . ) using data from the training set (e.g., member data for members 1-3000). For each distinct value of C, we obtain a parameter set, which we then evaluate using a validation objective function based on the validation set (e.g., member data for members 3001-4000). The parameters (and corresponding value of C) which achieve the highest validation objective function are returned as the optimal parameters (and hyperparameter) for the model. For this example, a reasonable validation objective function is the following:

$$L'(w,b)=\Sigma_{i=m+1,\ldots,M} \log P(y^{(i)}|x^{(i)};w,b) \quad (3).$$

Here, $x^{(m+1)}$ through $x^{(M)}$ correspond to the multidimensional vectors of features for the validation data. Note that the validation objective function does not include a regularization term, unlike the objective function (2).

In some embodiments, the data set is divided into several portions, and training and validation are repeated several times using selected combinations of the portions as the training sets or validation sets. For example, the same set of information for 4000 members may be divided into 4 portions of 1000 members each, and training/validation may be repeated 4 times, each time using a different set of member information for 1000 members as the validation set and the rest of the member information as the training set.

In some embodiments, a decision tree is generated as the model for predicting a phenotype such as PD. A decision tree model for predicting outcomes associated with a genotype can be created from a matrix of genotypic, family history, environmental, and outcome data. The member information example shown in FIG. 4 can also be used to generate the decision tree. The model can be generated with a variety of techniques, including ID3 or C4.5. For example, using the ID3 technique, the tree is iteratively constructed in a top-down fashion. Each iteration creates a new decision junction based on the parameter that results in the greatest information gain, where information gain measures how well a given attribute separates training examples into targeted classes. In other cases, the structure of the decision tree may be partially or completely specified based on manually created rules in situations where an automated learning technique is infeasible In some embodiments, the decision tree model is validated in the same way as the logistic regression model, by training and evaluating the model (retrospectively or prospectively) with a training set of individuals (e.g., members 1-3000) and an independent validation set (e.g., members 3001-4000).

In some embodiments, the model determination process accounts for genetic inheritance and the correlation of genetic information with family history information. There are various cancer studies showing that certain mutated genes are inherited according to Mendelian principles and people with mutations in these genes are known to be at significantly higher risk for certain types of disease (such as familial prostate cancer). In other words, possession of such mutated genes and having family members that have the disease are highly correlated events. The model, therefore, should account for such correlation.

Figure 5:
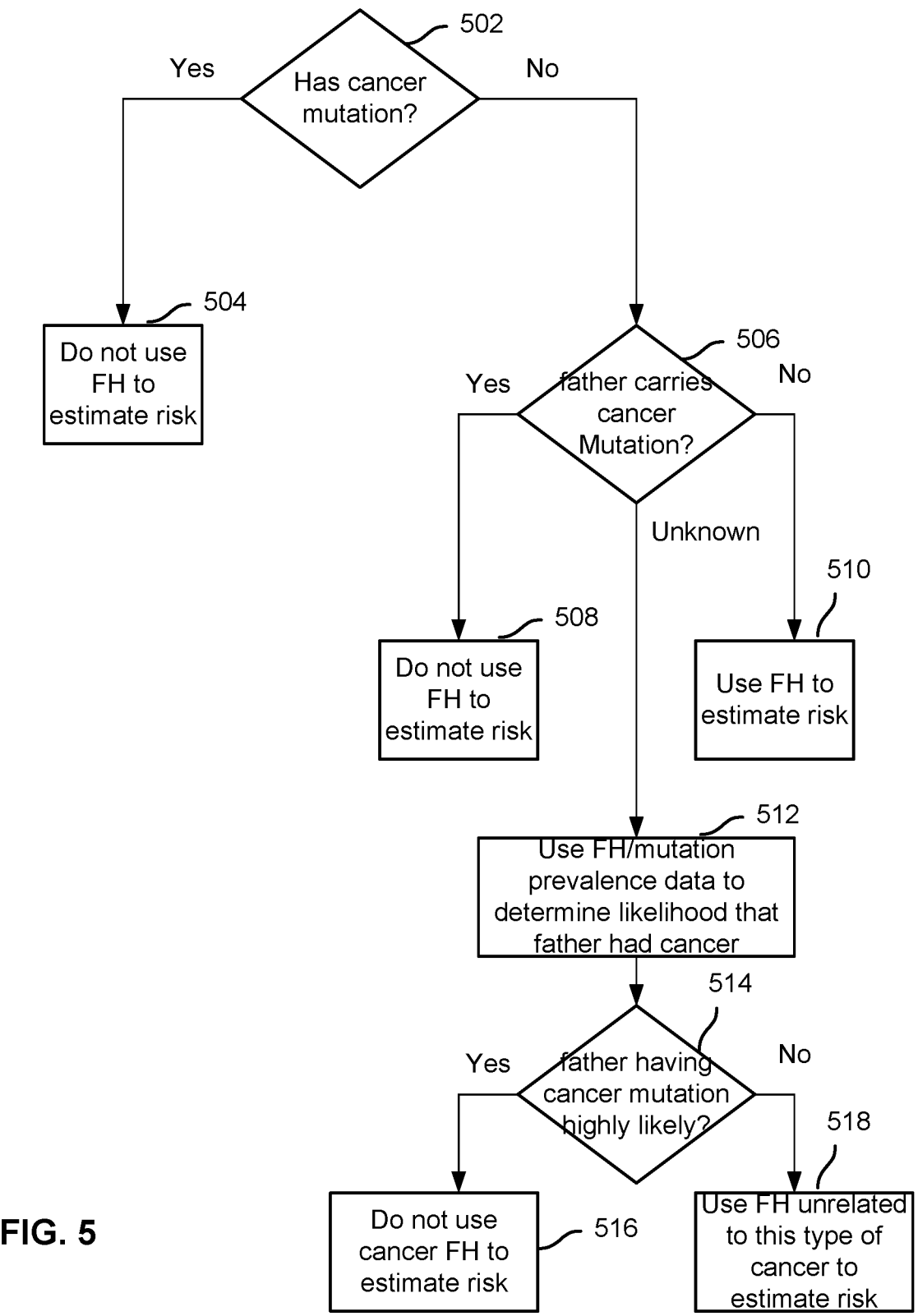
FIG. 5 is a diagram illustrating an example of a simplified decision tree.

FIG. 5 is an example of a simplified, manually-constructed decision tree that uses expert rules to approximately account for the correlation between the status of certain deleterious and highly penetrant genes that are highly correlated with a specific type of disease, and family history. The techniques described herein are generally applicable to various types of highly penetrant genetic mutations linked to certain diseases. For purposes of example, it is assumed that the mutated gene is highly correlated with a specific type of cancer that commonly occurs in men (e.g., prostate cancer). In this embodiment, the status of the specific deleterious mutations (also referred to as the cancer mutations) is used to determine whether to use the member's family history, in particular the history of having the specific type of cancer on the father's side, to predict the member's risk of developing the specific type of cancer. A primary assumption of this simplified model is that the specific type of cancer risk is modified by known deleterious mutations and by a large set of unknown mutations in other genes. The cancer mutations may be assayed directly using a genotyping technology. The influence of unknown mutations can only be indirectly measured by measuring family history for the disease. In more sophisticated models, the presence of common, low-penetrance mutations would also be included in the calculation.

At the first level, the tree splits into two branches according to whether the member has been positively tested for deleterious cancer mutations (502). If the member has a deleterious cancer mutation, his risk for the specific type of cancer (referred to as cancer risk in this example) is significantly increased due to this risk factor. In comparison, family history of whether the member's father had the specific type of cancer is assumed to have minimal additional effect on the member's cancer risk and is therefore not included in estimating the member's risk (504). This is because if the father had this type of cancer, it is very likely that the father's cancer was caused by the highly penetrant cancer mutation; therefore, this piece of information would not add significantly to the member's already elevated risk. Accordingly, in the simplified model, the father's history of having the specific type of cancer is omitted when the member carries a deleterious cancer mutation. In more complex models, the father's history of having the specific type of cancer may be accounted for even if the member carries a deleterious cancer mutation (e.g., the fact that the father had this type of cancer will increase the member's risk by a small percentage, regardless of whether the member carries a deleterious cancer mutation).

If, however, the member does not carry a deleterious cancer mutation, at the next level of the tree, a determination is made on whether the member's father carries the cancer mutation (506). If the father carries the cancer mutation, the father's family history (e.g., the father's brothers also had this type of cancer) is likely to be correlated with the presence of the cancer mutation in the family, which should not significantly affect the member's own cancer risk calculations given that any elevated risk due to the cancer mutation is already ruled out for the member. Thus, additional family history on the father's side is not used to estimate the member's risk (508).

If, however, the member's father also has no cancer mutation, then the family history should be used to estimate the member's cancer risk (510), based on the assumption that there may be other risk-modifying genes that are not yet identified but whose influence is detectable indirectly by noting a family history of the disease. In some embodiments, a first-degree relative (e.g., the father) with the disease is thought to increase the member's risk 4-fold, and a second-degree relative (e.g., an uncle) with the disease is thought to increase the member's risk 2-fold. The increase in risk attributable to the presence of disease in a relative can be estimated empirically by collecting data on disease prevalence in related and unrelated individuals.

If the father's cancer mutation status is unknown, family history (e.g., an autosomal dominant inheritance pattern such as multiple siblings having the type of cancer) and/or mutation prevalence data (e.g., the prevalence of the cancer mutations in a particular ethnic group) is used to determine how likely the father is to carry a deleterious cancer mutation (512). In this simplified model, if it is likely that the father (and therefore the father side of the family) carries a deleterious cancer mutation, then the model does not further require (or gives less weight to) cancer related family history on the father's side for making the risk prediction (516), since it is likely that the father's cancer was caused by the cancer mutation and it is already known that the member has not inherited the cancer mutation. If, however, it is unlikely that the father carries the cancer mutation, then the model requires (or gives full weight to) family history unrelated to the specific type of cancer on the father's side to estimate risk (518), since it tends to reveal the influence of other unidentified risk-modifying genes.

As can be seen from the example above, in a simplified model, when genetic information highly predictive of the phenotype is present (e.g., carrying a deleterious cancer mutation is highly predictive of certain type of cancer), the model does not further require family history information that is correlated with the phenotype (e.g., whether the father carries the deleterious cancer gene) to make the prediction. In some embodiments, more complex models take the correlated family history into consideration for making the prediction, but account for the correlation by giving less weight to the correlated family history information.

A trained and validated model for predicting a phenotype can be used to predict an individual's likelihood of exhibiting the phenotype. In some embodiments, an individual's information (e.g., the individual's genetic, family, and environmental information) is input and applied to the model (e.g., the regression model or the decision tree described above) to derive the predicted result. In some embodiments, the predicted result is compared with a certain threshold. If the predicted result exceeds the threshold, the system may provide the individual with additional feedback or suggestions such as getting additional testing that more precisely targets the genotype in question and requesting the user to provide additional phenotypic, family, and/or environmental information to improve the prediction, etc. If the individual provides the additional information requested, the prediction process may be re-executed while taking into account the additional information.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A network-based computer system comprising one or more processors and one or more memories, wherein the one or more processors are configured to:
   retrieve genetic information and additional information of a plurality of members of a personal genetic service from the one or more memories, wherein the additional information of the plurality of members comprises environmental information and phenotypic information of a phenotype of interest, and wherein the additional information of the plurality of members was received over a computer network through one or more network interfaces from one or more client devices; and
   train a machine-learning model by fitting one or more models to the genetic information and additional information of the plurality of members, wherein each of the one or more models is configured to receive as model input genetic information and environmental information of an individual, and provide as model output a prediction of the individual having or developing the phenotype of interest.

2. The system of claim 1, wherein the one or more client devices are configured to: (i) display a website to a user, (ii) receive environmental information and phenotypic information provided by the user via the website, or (iii) send the environmental information and phenotypic information over a network interface to one or more server computers.

3. The system of claim 2, wherein the computer system comprises the one or more client devices and the one or more network interfaces.

4. The system of claim 1, wherein the one or more processors are configured to apply the machine-learning model to a member of the personal genetic service by:
   retrieving genetic information of the member;
   retrieving additional information of the member comprising environmental information, wherein the additional information of the member was received through one of the network interfaces from a client device;
   inputting the genetic information of the member and the additional information of the member to the machine-learning model; and
   sending to the client device a prediction of the member having or developing the phenotype of interest obtained using the machine-learning model.

5. The system of claim 1, wherein:
   the additional information further comprises family history information; and
   the machine-learning model is configured to receive as additional input family history information of the individual.

6. The system of claim 5, wherein the family history information includes phenotypic information and genetic information of one or more family members of the plurality of members.

7. The system of claim 1, wherein:
   the additional information further comprises age; and
   the machine-learning model is configured to receive as additional input age of the individual.

8. The system of claim 1, wherein the machine-learning model comprises a regression model, a decision tree model, or a support vector machine model.

9. The system of claim 8, wherein the machine-learning model comprises a logistic regression model.

10. The system of claim 1, wherein training the machine-learning model comprises a cross-validation process comprising:
training a plurality of models using data of a training subset of members selected from the plurality of members, the plurality of models being fitted to the data of the training subset;
applying the plurality of models to data of a validation subset of members selected from the plurality of members to evaluate a performance of each of the plurality of models on the validation subset of members, wherein members of the training subset are different from members of the validation subset; and
selecting a model from the plurality of models based on the performance of the model from the plurality of models.

11. The system of claim 10, wherein the selected model has the highest performance among the plurality of models on the validation subset of members.

12. The system of claim 1, wherein the machine-learning model receives as input additional phenotypic information of one or more phenotypes other than the phenotype of interest.

13. The system of claim 1, wherein the prediction of the individual having or developing the phenotype of interest is selected from the group consisting of: a probability of the individual having or developing a disease over the course of the individual's lifetime, a probability of the individual having or developing a disease occurring within a specific time frame, and a probability of the individual currently having the disease.

14. The system of claim 1, wherein the prediction of the individual having or developing the phenotype of interest comprises an estimate of a value of a quantitative measurement, or an estimate of a distribution of likely measurements.

15. The system of claim 1, wherein the phenotype of interest is a disease.

16. The system of claim 1, wherein the phenotype of interest is a non-disease related trait.

17. A network-based computer system comprising one or more processors and one or more memories, wherein the one or more processors are configured to:
retrieve genetic information of a member of a personal genetic service from the one or more memories;
retrieve additional information of a member of a personal genetic service from the one or more memories, wherein the additional information of the member comprises environmental information, and wherein the additional information of the member was received over a computer network through one or more network interfaces from a client device;
inputting the genetic information of the member and the additional information of the member to a machine-learning model, wherein the machine-learning model has been trained by fitting one or more models to genetic information and additional information of a plurality of members, wherein additional information of the plurality of members comprises environmental information and phenotypic information of a phenotype of interest, wherein each of the one or more models is configured to receive as input genetic information and environmental information of an individual, and provide as output a prediction of the individual having or developing the phenotype of interest; and
outputting a prediction of the member having or developing the phenotype of interest using the machine-learning model.

18. The system of claim 17, wherein the client device is configured to: (i) display a website to the member, (ii) receive environmental information provided by the member via the website, or (iii) send the environmental information over a network interface to one or more server computers.

19. The system of claim 18, wherein the website is configured to display a probability of the member having or developing the phenotype of interest.

20. The system of claim 17, wherein:
the additional information of the plurality of members further comprises family history information; and
the machine-learning model is configured to receive as additional input family history information of the individual.

21. The system of claim 20, wherein the family history information includes phenotypic information and genetic information of one or more family members of the plurality of members.

22. The system of claim 20, wherein the additional information of the member comprises family history information.

23. The system of claim 17, wherein the additional information of the plurality of members was received over a computer network through one or more network interfaces from one or more client devices.

24. The system of claim 17, wherein the machine-learning model comprises a regression model, a decision tree model, or a support vector machine model.

25. The system of claim 24, wherein the machine-learning model comprises a logistic regression model.

26. The system of claim 17, wherein the phenotype of interest is a disease or a non-disease related trait.

27. A computer program product comprising one or more computer-readable non-transitory storage media having stored thereon computer-executable instructions that, when executed by one or more processors of a computer system, cause the computer system to:
obtain genetic information and additional information of a plurality of members of a personal genetic service, wherein the additional information of the plurality of members comprises environmental information and phenotypic information of a phenotype of interest, and wherein the additional information of the plurality of members was received over a computer network through one or more network interfaces from one or more client devices; and
train a machine-learning model by fitting one or more models to the genetic information and additional information of the plurality of members, wherein each of the one or more models is configured to receive as input genetic information and environmental information of an individual, and provide as output a prediction of the individual having or developing the phenotype of interest.

28. A method implemented using a network-based computer system comprising one or more processors, a network interface, and one or more memories, the method comprising:
retrieving, by the computer system, genetic information and additional information of a plurality of members of a personal genetic service from the one or more memories, wherein the additional information of the plurality of members comprises environmental information and phenotypic information of a phenotype of interest, and wherein the additional information of the plurality of members was received over a computer network through one or more network interfaces from one or more client devices; and training, by the one or more processors, a machine-learning model by fitting one or more models to the genetic information and additional information of the plurality of members, wherein each of the one or more models is configured to receive as input genetic information and environmental information of an individual, and provide as output a prediction of the individual having or developing the phenotype of interest.

* * * * *